(12) United States Patent
Watanabe et al.

(10) Patent No.: US 9,365,592 B2
(45) Date of Patent: *Jun. 14, 2016

(54) BONDING COMPOSITION

(71) Applicant: BANDO CHEMICAL INDUSTRIES, LTD., Kobe-shi, Hyogo (JP)

(72) Inventors: Tomofumi Watanabe, Kobe (JP); Kenji Shimoyama, Kobe (JP)

(73) Assignee: BANDO CHEMICAL INDUSTRIES, LTD., Kobe-Shi, Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/434,901

(22) PCT Filed: Oct. 3, 2013

(86) PCT No.: PCT/JP2013/005906
§ 371 (c)(1),
(2) Date: Apr. 10, 2015

(87) PCT Pub. No.: WO2014/057633
PCT Pub. Date: Apr. 17, 2014

(65) Prior Publication Data
US 2015/0252060 A1    Sep. 10, 2015

(30) Foreign Application Priority Data

Oct. 12, 2012   (JP) ................. 2012-226774

(51) Int. Cl.
| | | |
|---|---|---|
| *C07F 1/00* | (2006.01) | |
| *C09J 1/00* | (2006.01) | |
| *B22F 9/24* | (2006.01) | |
| *B82Y 30/00* | (2011.01) | |
| *B22F 1/00* | (2006.01) | |
| *B23K 35/30* | (2006.01) | |
| *B23K 35/02* | (2006.01) | |
| *B22F 1/02* | (2006.01) | |
| *B23K 35/22* | (2006.01) | |

(52) U.S. Cl.
CPC ... *C07F 1/00* (2013.01); *B22F 1/00* (2013.01); *B22F 1/0062* (2013.01); *B22F 1/02* (2013.01); *B22F 9/24* (2013.01); *B23K 35/0244* (2013.01); *B23K 35/22* (2013.01); *B23K 35/3006* (2013.01); *B23K 35/3013* (2013.01); *B82Y 30/00* (2013.01); *C09J 1/00* (2013.01)

(58) Field of Classification Search
CPC ...................................... C07F 1/00; C09J 1/00
USPC ......................................................... 556/110
See application file for complete search history.

(56) References Cited

U.S. PATENT DOCUMENTS

| | | |
|---|---|---|
| 2009/0236404 A1 | 9/2009 | Yamakawa et al. |
| 2012/0048426 A1 | 3/2012 | Ishizaki |
| 2014/0312285 A1* | 10/2014 | Takesue ............... B22F 1/0062 252/514 |

FOREIGN PATENT DOCUMENTS

| | | |
|---|---|---|
| JP | 4-146975 A | 5/1992 |
| JP | 2008-63688 A | 3/2008 |
| JP | 2011-95244 A | 5/2011 |
| JP | 2012-46779 A | 3/2012 |
| WO | 2007/034833 A1 | 3/2007 |
| WO | 2008/062548 A1 | 5/2008 |
| WO | 2012/105682 A1 | 8/2012 |

OTHER PUBLICATIONS

International Search Report dated Nov. 5, 2013, issued in corresponding application No. PCT/JP2013/005906.

* cited by examiner

*Primary Examiner* — Porfirio Nazario Gonzalez
(74) *Attorney, Agent, or Firm* — Westerman, Hattori, Daniels & Adrian, LLP

(57) ABSTRACT

To provide a bonding composition where high joint strength can be obtained due to joining at a comparatively low temperature and under a pressureless condition, and, that is also equipped with thermal resistance that is difficult to cause a reduction of joint strength due to decomposition, deterioration and/or the like of a resin component at the time of an increase of an operating temperature, and to provide a bonding composition particularly containing metallic particles. A bonding composition containing inorganic metallic particles and organic components including unsaturated hydrocarbon and amine with 4 to 7 of carbon number

14 Claims, No Drawings

BONDING COMPOSITION

TECHNICAL FIELD

The present invention relates to a bonding composition containing inorganic particles and organic components attached to at least part of the surfaces of the inorganic particles.

BACKGROUND TECHNOLOGY

In order to mechanically and/or electrically and/or thermally join a metallic component with a metallic component, solder, a silver paste, an anisotropically conductive film and the like are used. These anisotropically conductive adhesive, silver paste and anisotropically conductive film are not only for joining metallic components, but can be used for joining a ceramic component(s), a resin component(s) and the like. For example, joining of a light-emitting element, such as LED, to a substrate, joining of a semiconductor chip to a substrate, further joining of the substrates to a heat dissipation member and the like are exemplified.

Among them, an adhesive including solder and a conductive filler made from metal, a paste and a film are used for joining at a portion requiring electric connection. In addition, since metal has high thermal conductivity in general, these additive including solder and a conductive filler, paste and film may be used in order to increase heat dissipation, as well.

In the meantime, for example, when an illumination device or a light-emitting device with high intensity is manufactured using a light-emitting element, such as LED, or when a semiconductor device is manufactured using a semiconductor element that is referred to as a power device to efficiently run at a high temperature, a caloric value tends to rise. Although an attempt to improve an efficiency of the device or the element to reduce heat generation is conducted, a sufficient result has not been achieved under the present circumstances, and it is in the present situation where the operating temperature of the device and the element is increased.

Further, from a viewpoint to prevent damage to the device upon joining, a joint material that can secure sufficient joint strength at a low joining temperature (for example, 300° C. or less) is in demand. Therefore, although thermal resistance to withstand a decrease in a low joining temperature, and, a rise of operating temperature due to operation of the device after being joined and to enable the maintenance of sufficient joint strength is in demand in a joint material for joining a device, an element or the like, but conventional joint materials often cannot handle the situation under such conditions sufficiently. For example, solder joins members via a process to heat metal to its melting point or higher (reflow process), and since a melting point is unique to its composition in general, if a heatproof temperature is attempted to be increased, a heating (joining) temperature is also increased.

In addition, when several layers of elements or substrates are superposed and joined using solder, it is necessary to be via heating process by the number of times equal to the number of layers to be superposed, and in order to prevent fusion of the already joined parts, it is necessary to reduce a melting point (joining temperature) of the solder that is used in the next joining, and the number of types of solder composition equal to the number of the layers to be superposed becomes required, and handling becomes complicated.

In the other hand, in a conductive adhesive, a silver paste and an anisotropically-conductive film, although members are joined by utilizing thermal curing of epoxy resin or the like to be contained, if the operating temperature of the obtained device or element is increased, the resin component can be decomposed or deteriorated. For example, in Patent Literature 1 (Japanese Patent Application Laid-Open No. 2008-63688), particulates that are designed to obtain higher joint strength when members to be joined are joined using a chief material of the joint material has been proposed, but a problem about decomposition or deterioration of a resin component at the time of increasing the operating temperature has not been eliminated yet.

Further, solder containing lead has been conventionally used for high-temperature solder that is used at a high operating temperature. Since lead has toxic properties, a trend to lead-free solder is remarkable. Since there is no other alternative material for the high-temperature solder, lead solder is still used, but a joint material without using lead is desired from a viewpoint of environmental issues.

Recently, as an alternative material for the high-temperature solder, a joint material using metallic nanoparticles focus upon noble metals, such as silver or gold, has been developed (for example, Japanese Patent Application Laid-Open No. 2012-046779). However, in order to accomplish joining using the metallic nanoparticle is accomplished, it is necessary to perform pressure joining under inert atmosphere at 300° C. to 350° C., and a decrease in a joining temperature and no pressurization are issues.

PRIOR ART LITERATURES

Patent Literatures

Patent Literature 1: Japanese Patent Application Laid-Open No. 2008-63688
Patent Literature 2: Japanese Patent Application Laid-Open No. 2012-046779

SUMMARY OF THE INVENTION

Problem to be Solved by the Invention

In light of the circumstances above, the objective of the present invention is to provide a bonding composition that can obtain high joint strength by joining at a comparatively low temperature and under no pressure, and, that is also equipped with thermal resistance, which hardly causes a reduction of the joint strength due to decomposition or deterioration of the component region at the time of increasing the operating temperature, and to provide particularly a bonding composition containing metallic particles.

Means for Solving the Problem

The inventors of the present application, as a result of keen study about the composition of a bonding composition to accomplish the objective, have discovered that it would be extremely effective to accomplish the objective by containing inorganic metallic particles and organic components attached to at least part of surfaces of the inorganic metallic particles, and, by optimizing the organic components, and he has accomplished the present invention.

In other words, the present invention provides a bonding composition that contains inorganic metallic particles and organic components including unsaturated hydrocarbon and amine with 4 to 7 of carbon number.

For particle size of the inorganic metallic particles composing the bonding composition of the present invention, a nanometer-size particle so as to cause depression of the melting point, desirably 1 nm to 200 nm, is appropriate, but it is also possible to add micron-meter-size particles as needed. In this case, joining is accomplished by lowering the melting point of the nanometer-size particles around the micrometer-size particles.

In order to stably store the nanometer-size inorganic metallic particles indicating melting-point depression capability, a certain amount of organic components on the surfaces of the inorganic metallic particles is required, and the organic components in the present invention include unsaturated hydrocarbon and amine with 4 to 7 carbon number.

In other words, in the bonding composition of the present invention, amine with 4 to 7 of carbon number is used as a so-called dispersant. Low-temperature baking type inorganic metallic particles can be obtained by using low-boiling-point amine with comparatively small number of carbon chains. Provided, however, that the bonding composition of the present invention can include other amine than one having 4 to 7 of carbon number. As a compositional molar ratio at the time of synthesizing inorganic metallic particles, when metallic salt is 1, amine with 4 to 7 of carbon number can be optionally selected within the range of 0.001 to 30, but it is preferably 0.005 to 20 and is further preferably 0.01 to 10.

Unsaturated hydrocarbon out of the organic components has a double bond, and has effects to improve dispersibility of the inorganic metallic particles into an organic solvent due to the steric structure, and to suppress agglomeration of the inorganic metallic particles with each other. Further, in the amine, its functional group is adsorbed onto the surfaces of the inorganic metallic particles with modest strength, and the amine contributes to stability of the inorganic metallic particles in a stored condition in order to prevent mutual contact of the inorganic metallic particles. Further, it is believed that fusion of the inorganic metallic particles with each other and joining between the inorganic metallic particles and a substrate are accelerated by migration or volatilization from the surfaces of the inorganic metallic particles at a joining temperature.

The unsaturated hydrocarbon preferably has a hydroxyl group. A hydroxyl group and a carboxyl group tend to be coordinated on the surfaces of the inorganic metallic particles, and can enhance an agglomeration suppressive effect of the inorganic metallic particles. Further, due to coexistence of a hydrophobic group and a hydrophilic group, an effect to dramatically enhance wettability between the bonding composition and a joining substrate also exists. Furthermore, a functional group is not limited to a hydroxyl group, but it can be a carboxyl group or the like.

The unsaturated hydrocarbon is preferably ricinoleic acid. Ricinoleic acid has a carboxyl group and hydroxyl group, and it is believed to have an effect to be adsorbed onto the surfaces of the inorganic metallic particles to uniformly disperse the inorganic metallic particles and to have another effect to accelerate fusion of the inorganic metallic particles. Heat and oxygen are required for volatizing organics, and the organics on the surfaces of the inorganic metallic particles are also similar. It is believed that the ricinoleic acid's effect to accelerate baking of the inorganic metallic particles is caused by oxygen in a carboxyl group and a hydroxyl group to accelerate volatilization and decomposition of organic substances attached on the surfaces of the inorganic metallic particles.

Further, since ricinoleic acid starts decomposing around 200° C., thermogravimetric reduction of organic components including ricinoleic acid and sintering shrinkage of particles progress at the right time, and pressureless joining can be accomplished. As a result, a dense joining layer with less residual organic components can be obtained, and a joined part having sufficient strength can be formed under a pressureless condition.

Ricinoleic acid can be added as a dispersant to coat the surfaces of the inorganic metallic particles at the time of synthesizing the inorganic metallic particles, and can be added as an additive after purification of the inorganic metallic particles. As a compositional molar ratio at the time of synthesizing the inorganic metallic particles, when metallic salt is 1, unsaturated hydrocarbon can be optionally selected within a range of 0.001 to 10, and it is preferably 0.005 to 5 and more preferably 0.01 to 3. As a ratio by weight in the case of adding after purification of the inorganic metallic particles, ranges of inorganic metallic particles (including organics coating the surfaces)/unsaturated hydrocarbon can be optionally selected from 99/1 to 50/50, and it is preferably 98/2 to 70/30, and more preferably 97/3 to 75/25.

Herein, for example, a case when the bonding composition of the present invention is applied onto an alumina ceramics substrate with a gold-plated surface, and the same substrate is placed over it and an obtained laminated body is heated at 300° C. is simulated. On the occasion of gradually increasing a temperature of the bonding composition by heating, organic components that are comparatively volatile are volatilized by the time of reaching 200° C. Substantial amounts of organic components still remain in this stage, and inorganic metallic particles are not aggressively fused with each other, but the bonding composition in the applied state still has flexibility. Consequently, even if organic components become gas to be volatilized and a portion (passage) like a hollow after the gas has passed is created, the bonding composition in the periphery is moved and the portion will be filled. Then, a connection of the fused inorganic metallic particles becomes integral and sufficient joint strength is obtained; therefore, conductivity and thermal conductivity are also improved.

In addition, in the bonding composition of the present invention, although amino groups in one molecule with 4 to 7 of carbon number have a comparatively high polarity and interaction due to a hydrogen bond, a portion other than these functional groups has a comparatively low polarity. In addition, the amino groups tend to indicate alkaline properties, respectively. Therefore, when amine with 4 to 7 of carbon number is localized (attached) to at least part of the surfaces of the inorganic metallic particles in the bonding composition of the present invention (in other words, coats at least part of the surfaces of the inorganic metallic particles), the organic components and the inorganic metallic particles can sufficiently have affinity, and the agglomeration between the inorganic metallic particles is prevented.

Further, even when a dispersion medium is added as needed, because the organic components act as a dispersant, a dispersion state of the inorganic metallic particles in the dispersion medium is remarkably improved. In other words, according to the joining component of the present invention, because a specific combination of organic substances is contained, the inorganic metallic particles are difficult to be agglomerated, and dispersibility of the inorganic metallic particles is excellent while coating with a film, and uniformly-fused and strong joint strength is obtained.

Herein, the bonding composition of the present invention, in other words, is a composition consisting primarily of colloidal particles made from the inorganic metallic particles and the organic substances, and it can be a colloidal dispersion liquid further containing a dispersion medium. Although "dispersion medium" is for dispersing the colloidal particles in the dispersion liquid, a portion of the constituents in the colloidal particles can be dissolved in the "dispersion medium". Furthermore, "primary component" means a component that is contained the most among the constituents.

Further, in the bonding composition of the present invention, it is preferable that the inorganic metallic particles are at least one type of metallic particles out of gold, silver, copper, nickel, bismuth, tin and platinum group elements. If the joining component with such configuration is used, superior joint strength and heat resistance can be obtained. In addition, the bonding composition of the present invention is preferably used for joining of metals with each other.

According to the present invention, the bonding composition where high joint strength can be obtained even under a pressureless condition at a low joining temperature by containing inorganic metallic particles and organic components that are attached onto at least part of the surfaces of the inorganic metallic particles, and, by optimizing the organic components.

Hereafter, one preferred embodiment of the bonding composition of the present invention is described in detail. Furthermore, the description above merely indicates one embodiment of the present invention, and this does not limit the present invention, and any redundant explanations may be omitted.

(1) Bonding Composition

The bonding composition of the present embodiment is characterized by containing inorganic metallic components and organic components including unsaturated hydrocarbon and amine with 4 to 7 of carbon number. Hereafter, these components are explained, respectively.

(1-1) Inorganic Metallic Particle

The inorganic metallic particle in the bonding composition in the present embodiment is not particularly limited, but since conductivity of an adhesion layer obtained by using the bonding composition of the present embodiment can be improved, metal that has smaller ionization tendency (that is nobler) than zinc is preferable.

As such metal, for example, at least one type out of gold, silver, copper, nickel, bismuth, tin, iron and platinum group elements (ruthenium, rhodium, palladium, osmium, iridium and platinum) is exemplified. As the metal above, it is preferable to be at least one type of metallic particle to be selected from a group constituting of gold, silver, copper, nickel, bismuth, tin and platinum group elements, and in addition, at least one type out of copper, metal with smaller ionization tendency (nobler) than copper, i.e., gold, platinum, silver and copper is preferable. These metals can be used singularly or used in combination with two types or more, and as a combining method, there are a case of using alloy particles containing a plurality of metals and another case of using metallic particles having a core-shell structure or multi-layered structure.

For example, when silver particles are used as the inorganic metallic particles in the bonding composition, conductivity of the adhesion layer formed by using the bonding composition of the present embodiment is improved, but considering a problem about migration, it can make it difficult to cause migration by using a bonding composition made from silver and other metals. As such "other metals", metal where its ionization series is nobler than that of hydrogen, i.e., gold, copper, platinum and palladium are preferable.

Mean particle size of the inorganic metallic particles (or inorganic metallic colloidal particles) in the bonding composition of the present embodiment is not particularly limited as long it is within a range not impairing the effects of the present invention, and it is preferable to have mean particle size so as to cause depression of a melting point, and for example, a range of 1 nm to 200 nm is preferable. A range of 2 nm to 100 nm is further preferable. If the mean particle size of the inorganic metallic particles is 1 nm or greater, a bonding composition that can form an excellent adhesion layer can be obtained, and this is practicable because manufacturing cost of the inorganic metallic particles will not be increased. Further, if the mean particle size is 200 nm or less, it is preferable because it is difficult for dispersibility of the inorganic metallic particles to be changed over time.

Further, it is also possible to adjunctively add micrometer-size inorganic metallic particles as needed. In that case, nanometer-size inorganic metallic particles can be joined by lowering a melting point around the periphery of micrometer-size inorganic metallic particles.

Furthermore, the particle size of the inorganic metallic particles in the bonding composition of the present invention is not always constant. Further, when the bonding composition contains a dispersion medium, a resin component, an organic solvent, a thickener, a surface tension regulator or the like, there is a case where organic metallic colloidal particle components with mean particle size exceeding 200 nm are included, but as long as these are components that do not cause agglomeration or do not remarkably impair the effect of the present invention, particle components having mean particle size exceeding 200 nm may be included.

Herein, the particle size of the inorganic metallic particles in the bonding composition (metallic colloidal dispersion liquid) of the present embodiment can be measured using dynamic light scattering, small-angle X-ray scattering technique or wide-angle X-ray diffraction technique. In order to demonstrate depression of a melting point of the nanosize metallic particles, crystallite diameter obtained using the wide-angle X-ray diffraction technique is appropriate. For example, in the wide-angle X-ray diffraction technique, more specifically, the crystallite diameter can be measured within the range of 30° to 80° of 2θ with a diffraction technique using RINT-Ultima III manufactured by Rigaku Corporation. In this case, samples should be rolled thinly so as to be a flat surface over a glass plate having a recess with approximately 0.1 mm to 1 mm of depth in the center. Further, crystallite diameter (D) calculated by assigning a half-value width of the obtained diffraction spectrum to the following Scherrer equation using JADE manufactured by Rigaku Corporation should be particle size:

$$D = K\lambda / B \cos \theta$$

Herein, K: Scherrer constant (0.9), λ: wavelength of X-ray, B: half-value width of diffraction line and θ: Bragg angle.

(1-2) Organic Components Attached Onto at Least Part of Surfaces of Inorganic Metallic Particles In the bonding composition of the present embodiment, the organic components that are attached onto at least part of the surfaces of the inorganic metallic particles; i.e., "organic components" in the inorganic metallic colloidal particles substantially compose inorganic metallic colloidal particles as a so-called dispersant along with the inorganic metallic particles. This is a concept where the organic components do not include trace organics originally contained in the metal as impurities, trace organics that are mixed in manufacturing process to be described later and attached to a metal component(s), and a trace amount of organics attached onto the inorganic metallic particles, such as a residual reducing agent or a residual dispersant that could not be removed in a washing process. Furthermore, the "trace" intends to be specifically, less than 1% by mass in the metallic colloidal particle.

The organic components are organics that coat the inorganic metallic particles to prevent agglomeration of the inorganic metallic particles, and, that enable the formation of the inorganic metallic colloidal particles, and the coating form is not particularly defined, but in the present embodiment, unsaturated hydrocarbon and amine with 4 to 7 of carbon number are included from a viewpoint of dispersibility, conductivity and the like. Furthermore, it is believed that these organic components are changed to anion or cation if these chemically or physically bind to the inorganic metallic particles, and in the present embodiment, ions, complexes and the like derived from these organic components are included in the organic components above.

As amine with 4 to 7 of carbon number, as long as the carbon number is 4 to 7, both straight-chain and branched ones are acceptable, and it may have a side chain(s). For example, alkylamine (straight-chain alkylamine may have a side chain(s)), such as butylamine, pentylamine, hexylamine; cycloalkylamine, such as cyclopentylamine or cyclohexylamine; primary amine, such as allylamine, such as aniline; secondary amine, such as dipropylamine, dibutylamine, piperidine or hexamethyleneimine; tertiary amine, such as tripropylamine, dimethyl propanediamine, cyclohexyldimethylamine, or pyridine, and the like are exemplified.

The amine with 4 to 7 of carbon number may be, for example, a compound containing a functional group, such as a hydroxyl group, a carboxyl group, an alkoxy group, a carbonyl group, an ester group or a mercapto group, other than amine. In this case, the carbon number in the functional group is not included in the carbon number of "amine with 4 to 7 of carbon number". Further, the number of nitrogen atoms derived from amine is preferably the number of functional groups other than amine or greater. Further, the amine may be used singularly, and can be used in combination with two types or more. In addition, a boiling point under ordinary pressure is preferably 300° C. or less, and is further preferably 250° C. or less.

The bonding composition of the present embodiment may contain a carboxylic acid within a range not impairing the effects of the present invention, in addition to the amine with 4 to 7 of carbon number. A carboxyl group in one molecule of a carboxylic acid has comparatively high polarity and easily causes interaction due to a hydrogen bond, but a portion other than these functional groups has comparatively low polarity. In addition, the carboxyl group tends to show an acidic property. Further, if the carboxylic acid is localized (attached) to/onto at least part of the surfaces of the inorganic metallic particles in the bonding composition of the present embodiment (i.e., if the carboxylic acid is coated on at least part of the surfaces of the inorganic metallic particles), the organic components and the inorganic metallic particles can sufficiently have affinity with each other, and the agglomeration between the inorganic metallic particles is prevented (dispersibility is improved).

As the carboxylic acid, a compound having at least one carboxyl group can be widely used, and for example, formic acid, oxalic acid, acetic acid, hexane acid, acrylic acid, octylic acid, oleic acid and the like are exemplified. A carboxyl group, which is a part of carboxylic acid, may form salt with a metallic ion. Furthermore, the metallic ion may contain two types or more of metallic ions.

The carboxylic acid may be, for example, a compound containing a functional group other than a carboxylic group, such as an amino group, a hydroxyl group, an alkoxy group, a carbonyl group, an ester group or a mercapto group. In this case, the number of carboxyl groups is preferably the number of functional groups other than carboxyl groups or greater. Further, the carboxylic acid can be used singularly, respectively, and can be used in combination with two types or more. In addition, a boiling point at ordinary temperature is preferably 300° C. or less, and is further preferably 250° C. or less. Further, amine and carboxylic acid form amide. Since the amide group is also moderately adsorbed onto the surfaces of silver particles, the organic components may contain an amide group.

The content of the organic components in the metallic colloid in the bonding composition of the present embodiment is preferably 0.5% to 50% by mass. If the content of the organic components is 0.5% by mass or greater, storage stability of the obtained bonding composition tends to be improved, and if it is 50% by mass or less, the conductivity of the bonding composition tends to be better. The more preferable content of the organic components is 1% to 30% by mass, and the further preferable component is 2% to 15% by mass.

As a composition ratio (mass) in the case of combining amine and carboxylic acid, the range of 1/99 to 99/1 can be optionally selected, and it is preferably 20/80 to 98/2, and is further preferably 30/70 to 97/3. Furthermore, for amine or carboxylic acid, a plurality of types of amines or carboxylic acids may be used, respectively.

As unsaturated hydrocarbon contained in the bonding composition of the present embodiment, for example, ethylene, acethylene, benzene, acetone, 1-hexene, 1-octene, 4-vinyl-cyclohexene, cyclohexanone, terpene-series alcohol, allyl alcohol, oleyl alcohol, 2-palmitoleic acid, petroselinic acid, oleic acid, elaidic acid, tianshic acid, ricinoleic acid, linoleic acid, linolelaidic acid, linolenic acid, arachidonic acid, acrylic acid, methacrylic acid, gallic acid, salicylic acid and the like are exemplified.

Among them, unsaturated hydrocarbon having a hydroxyl group is preferable. A hydroxyl group tends to be coordinated on the surfaces of the inorganic metallic particles, and agglomeration of the inorganic metallic particles can be suppressed. As unsaturated hydrocarbon having a hydroxyl group, for example, terpene-series alcohol, allyl alcohol, oleyl alcohol, tianshic acid, ricinoleic acid, gallic acid, salicylic acid and the like are exemplified. Preferably, it is an unsaturated fatty acid having a hydroxyl group, and for example, tianshic acid, ricinoleic acid, gallic acid, salicylic acid and the like are exemplified.

The unsaturated hydrocarbon is preferably ricinoleic acid. Ricinoleic acid has a carboxyl group and a hydroxyl group, and is adsorbed onto the surfaces of the inorganic metallic particles to uniformly disperse the inorganic metallic particles, and, accelerates fusion of the inorganic metallic particles.

In order to provide functions, such as moderate viscosity, adhesiveness, a drying property or printability, according to an intended use, optional components, such as a dispersion medium, an oligomer component that fulfills, for example, a role as a binder, a resin component, an organic solvent (part of solid content may be dissolved or dispersed), a surfactant, a thickener or a surface tension regulator, can be added to the bonding composition of the present embodiment. Such optional components are not particularly limited.

As the dispersion medium out of the optional components, various ones are usable within the range not impairing the effects of the present invention, and for example, hydrocarbon, alcohol and the like are exemplified.

As the hydrocarbon, aliphatic hydrocarbon, cyclic hydrocarbon and alicyclic hydrocarbon are exemplified, and these can be used singularly, respectively, and can be used in combination of two types or more.

As the aliphatic hydrocarbon, for example, saturated or unsaturated aliphatic hydrocarbon, such as tetradecane, octadecane, heptamethylnonane, tetramethylpentadecane, hexane, heptane, octane, nonane, decane, tridecane, methylpentane, normal paraffin or isoparaffin, is exemplified.

As the cyclic hydrocarbon, for example, toluene, xylene and the like are exemplified.

In addition, as the alicyclic hydrocarbon, for example, limonene, dipentene, terpinene, terpinene (also referred to as terpinene), nesol, cinene, orange flavor, terpinolene, terpinolene (also refer to as terpinolene), phellandrene, menthadiene, terebene, dihydrocymene, moslene, isoterpinene, isoterpinene (also referred to as isoterpinene), crithmene, kautschin, cajeputene, oirimen, pinene, turpentine, menthane, pinane, terpene, cyclohexane and the like are exemplified.

Further, alcohol is a compound containing one or more OH group(s) in the molecular structure, and aliphatic alcohol, cyclic alcohol and alicyclic alcohol are exemplified, and they can be used singularly, respectively, and can be used in a combination of two types of more. Further, part of OH groups may be induced to an acetoxy group within a range not impairing the effects of the present invention.

As the aliphatic alcohol, for example, saturated or unsaturated $C_{6-30}$ aliphatic alcohol, such as heptanol, octanol (such as 1-octanol, 2-octanol or 3-octanol), decanol (such 1-decanol), lauryl alcohol, tetradecyl alcohol, cetyl alcohol, 2-ethyl-1-hexanol, octadecyl alcohol, hexadecenol or oleyl alcohol, is exemplified.

As the cyclic alcohol, for example, cresol, eugenol and the like are exemplified.

In addition, as the alicyclic alcohol, for example, cycloalkanol, such as cyclohexanol; terpineol (including α, β and γ isomers, or any mixture of these); terpene alcohol (such as monoterpene alcohol), such as dihydroterpioneol; dihydroterpioneol, myrtenol, sobrerol, menthol, carveol, perillyl alcohol, pinocarveol, sobrerol, verbenol and the like are exemplified.

The content in the case of containing a dispersion medium in the bonding composition of the present invention should be adjusted according to a desired characteristic, such as viscosity, and the content of a dispersion medium in the bonding composition is preferably 1% to 30% by mass. In the case that the content of a dispersion medium is 1% to 30% by mass, an effect to adjust the viscosity in the range where it can be suitably used as a bonding composition can be obtained. The more preferable content of the dispersion medium is 1% to 20% by mass, and further preferable content is 1% to 15% by mass.

As the resin component, for example, polyester resin, polyurethane resin, such as blocked isocyanate, polyacrylate resin, polyacrylamide resin, polyether resin, melamine-series resin, terpene-series resin and the like can be exemplified, and these can be used singularly, respectively, and can be used in a combination with two types or more.

As the organic solvent, other than the ones exemplified as a dispersion medium, for example, methylalcohol, ethylalcohol, n-propylalcohol, 2-propylalcohol, 1,3-propanediol, 1,2-propanediol, 1,4-butanediol, 1,2,6-hexantriol, 1-ethoxy-2-propanol, 2-butoxyethanol, ethylene glycol, diethylene glycol, triethylene glycol, polyethylene glycol having weight-average molecular weight within a range between 200 to 1,000, propylene glycol, dipropylene glycol, tripropylene glycol, polypropylene glycol having weight-average molecular weight within a range between 300 and 1,000, N,N-dimethylformamide, dimethylsulfoxide, N-methyl-2-pyrrolidone, N,N-dimethylacetamide, glycerin, acetone and the like are exemplified, and these can be used singularly, and can be used in combination with two types or more.

As the thickener, for example, clay mineral, such as clay, bentonite or hectorite; for example, emulsion, such as polyester emulsion resin, acrylic emulsion resin, polyurethane emulsion resin or blocked isocyanate; cellulose derivatives, such as methylcellulose, carboxy methylcellulose, hydroxyl methylcellulose, hydroxylpropyl cellulose, hydroxylpropyl methylcellulose; polysaccharide, such as xanthane gum or guar gum, and the like are exemplified, and these can be used singularly, respectively, and can be used in a combination with two or more types.

A surfactant, which is different from the organic components as above described, may be added. In a multicomponent solvent-series metallic colloidal dispersion liquid, roughness on the coated surface and bias of solid content due to a difference in rates of volatilization at the time of drying easily occur.

A bonding composition that can suppress these disadvantages by adding a surfactant to the bonding composition of the present embodiment, and that can form a uniform conductive coating can be obtained.

A surfactant that is usable in the present embodiment is not particularly limited, and any of an anionic surfactant, a cationic surfactant and a nonionic surfactant can be used, and for example, alkyl benzene sulfonate, quaternary ammonium salt and the like are exemplified. Since an effect can be obtained with a small additive amount, a fluorochemical surfactant is preferable.

Furthermore, a method to adjust an amount of organic components within a predetermined range will be descried later, and adjustment by heating is simple. Further, it can be adjusted by adjusting an amount of organic components to be added on the occasion of manufacturing the inorganic metallic particles, and washing conditions and/or the number of washing times after the adjustment of the inorganic metallic particles may be changed. Heating can be conducted with an oven or an evaporator, and can be conducted under reduced pressure. In the case of heating under ordinary pressure, it can be conducted in the atmosphere or in an inert atmosphere, as well. In addition, amine (and carboxylic acid) can be added later for the purpose of fine adjustment of the amount of organic components.

The bonding composition of the present embodiment contains inorganic metallic colloidal particles where inorganic metallic particles to be described later become colloid as a primary component, and regarding the form of such inorganic metallic colloidal particles, for example, inorganic metallic colloidal particles constructed by attaching organic components on part of the surfaces of the inorganic metallic particles, inorganic metallic colloidal particles constructed by coating the surfaces with organic components using the inorganic metallic particles as core, inorganic metallic colloidal particles constructed by mixing those and the like are exemplified, but the form is not particularly limited. Among them, the inorganic metallic colloidal particles constructed by coating the surfaces with organic components using the inorganic metallic particles as core are preferable. A person of ordinary skills in the art pertaining to the present invention can appropriately prepare the inorganic metallic colloidal particles having the form above using the prior art in the field.

The bonding composition of the present embodiment is a fluent material consisting primarily of colloidal particles composed of inorganic metallic particles and organic components, and may contain organic components not constituting of inorganic colloidal particles, a dispersion medium, a residual reducing agent or the like, in addition to organic components constituting of inorganic metallic particles and inorganic metallic colloidal particles.

For viscosity of the bonding composition of the present embodiment, concentration of the solid content should be appropriately adjusted within a range not impairing the effects of the present invention, and for example, it should be within the viscosity of 0.01 Pa·s to 5,000 Pa·s, and the viscosity range of 0.1 Pa·s to 1,000 Pa·s is more preferable and the viscosity range of 1 Pa·s to 100 Pa·s is particularly preferable. A broader method can be applied as a method for applying the bonding composition on a substrate by setting the viscosity ranges.

As the method for applying the bonding composition on a substrate, for example, a method can be appropriately selected and adopted from any of dipping, a spray method, a bar coating technique, a spin coating technique, an inkjet technique, a dispenser technique, a pin transfer technique, an application method with a brush, a casting technique, a flexo technique, a gravure technique, an offset technique, transfer process, a hydrophobic-hydrophilic pattern technique, a syringe technique and the like.

The viscosity can be adjusted by controlling the particle size of inorganic metallic particles, controlling content of organics, adjusting additive amounts of a dispersion medium and other components, controlling a compounding ratio of each component, adding a thickener or the like. The viscosity of the bonding composition can be measured, for example, with a cone-plate viscometer (for example, Rheometer MCR301 manufactured by ANTON PAAR).

(2) Manufacturing of the Bonding Composition

Next, in order to manufacture the bonding composition containing inorganic metallic colloid of the present embodiment, inorganic metallic particles (inorganic metallic colloidal particles) coated with organic components are prepared as a main component.

Furthermore, a method for adjusting the amount of the organic components and a weight reduction rate is not particularly limited, but it is simple to adjust them by heating. Further, adjustment can be made by controlling the amount of organic components to be added on the occasion of producing the inorganic metallic particles, and washing conditions and the number of washing times after the adjustment of the inorganic metallic particles can be changed. The heating can be conducted with an oven, an evaporator or the like. A heating temperature can be within a range from approximately 50° C. to 300° C., and a heating time should be for several minutes to several hours. Heating can be conducted under reduced pressure. Heating under reduced pressure enables adjustment of an amount of the organics at a lower temperature. In the case of heating under ordinary pressure, it can be conducted in the atmosphere or in an inert atmosphere, as well. In addition, for the purpose of fine adjustment of the amount of organics, amine and carboxylic acid can be added later.

A method for preparing inorganic metallic particles coated with the organic components of the present embodiment is not particularly limited, but for example, a method where a dispersion liquid containing inorganic metallic particles is prepared, and next, the dispersion liquid is washed or the like is exemplified. As a step to prepare a dispersion liquid containing the inorganic metallic particles, for example, as mentioned below, metallic salt (or metallic ion) dissolved into a solvent should be reduced, and as the reduction procedures, procedures based upon a chemical reduction method should be adopted.

In other words, the inorganic metallic particles coated with the organic components can be prepared by reducing a raw material solution (part of components is not dissolved but can be dispersed) containing metallic salt of metal composing the inorganic metallic particles, organics as a dispersant, and a solvent (it is basically an organic-series, such as toluene, but it can contain water).

Due to this reduction, inorganic metallic colloidal particles where organic components as a dispersant are attached to at least part of the surfaces of the inorganic metallic particles can be obtained. This inorganic metallic colloidal particle can be supplied as the bonding composition of the present embodiment only as is, but the bonding composition made from inorganic metallic colloidal dispersion liquid can also be obtained by adding this to a dispersion medium in the step described later as needed.

As a starting material for obtaining the inorganic metallic particles coated with organics, various well-known metallic salts or its hydrates can be used, and for example, silver salts, such as silver nitrate, silver sulfate, silver chloride, silver oxide, silver acetate, silver oxalate, silver formate, silver nitrite, silver chlorate or silver sulfide; for example, gold salts, such as chlorauric acid, gold potassium chloride or gold sodium chloride; for example, platinum salts, such as chloroplatinic acid, platinum chloride, platinum oxide or potassium chloroplatinate; for example, palladium salts, such as palladium nitrate, palladium acetate, palladium chloride, palladium oxide or palladium sulfate, and the like are exemplified, but these cannot be particularly limited as long as they can be dissolved into an appropriate dispersion medium, and, are reducible. Further, these can be used singularly, and a plurality of them can be combined.

Further, a method to reduce these metallic salts in the raw material liquid above is not particularly limited, but for example, a method for using a reducing agent, a method for irradiating a light, such as ultraviolet rays, electron beams, ultrasonic or thermal energy, and the like are exemplified. Among them, the method for using a reducing agent is preferable from a viewpoint of easy operation.

As the reducing agent, for example, amine compounds, such as dimethylaminoethanol, methyldiethanolamine, triethanolamine, phenidone or hydrazine; for example, hydrogen compounds, such as sodium borohydride, hydrogen iodide or hydrogen gas; for example, oxides, such as carbon monoxide or sulfurous acid; for example, low valence metallic salts, such as ferrous sulfate, ferric oxide, ferrous fumarate, ferrous lactate, iron oxalate, ferric sulfide, tin acetate, tin chloride, tin chloride, tin diphosphate, tin oxalate, tin oxide or tin sulfate; for example, sugars, such as ethylene glycol, glycerin, formaldehyde, hydroquinone, pyrogallol, tannin, tannic acid, salicylic acid or D-glucose, and the like are exemplified, but they are not particularly limited as long as these are dissolved into a dispersion medium and can reduce the metallic salts. In the case of using the reducing agent above, the reduction reaction can be accelerated by adding a light and/or heat.

As a specific method to prepare metallic particles coated with organics using the metallic salt, the organic components, the solvent and the reducing agent, for example, a method where the metallic salt is dissolved into an organic solvent (for example, such as toluene) to prepare a metallic salt solution; organics as a dispersant are added to the metallic salt solution; and next, a solution where a reducing agent is dissolved is gradually instilled into [this mixture] or the like is exemplified.

A counterion(s) of the metallic salt, a residue of the reducing agent and a dispersant exist in the dispersion liquid containing the inorganic metallic particles coated with organic components as a dispersant as obtained above in addition to inorganic metallic particles, and electrolyte concentration of the entire liquid tends to be higher. Since a liquid in such condition has high conductivity, coagulation of inorganic metallic particles occurs, and it is easily precipitated. Alternatively, even though these are not precipitated, if the counterion(s) of the metallic salt, a residue of a reducing agent or an excessive dispersant or a more than necessary amount of excessive dispersant remains, the conductivity is likely to be deteriorated. Then, the inorganic metallic particles coated with organics can be certainly obtained by washing a solution containing the inorganic metallic particles and removing any excessive residues.

As the washing method, for example, a method to repeat a step to statically place a dispersion liquid containing the inorganic metallic particles coated with organics for a certain period of time, to add alcohol (such as methanol) and then stir [the mixed solution] again after a generated supernatant solution is removed, to place [the mixed solution] statically again for a certain period of time, and to remove a generated supernatant solution; and another method where centrifugal separation is conducted instead of placing statically; another method for demineralization with a ultrafiltration apparatus or ion-exchange equipment and the like are exemplified. The inorganic metallic particles coated with organics in the present embodiment can be obtained by removing an organic solvent with such washing.

Among the present embodiment, the inorganic metallic colloidal dispersion liquid can be obtained by mixing inorganic metallic particles and the dispersion medium explained in the present embodiment. The method for mixing such inorganic metallic particles coated with the organic substances with the dispersion medium is not particularly limited, and it can be conducted with a conventionally-known method using an agitator, a stirrer or the like. [The inorganic metallic colloidal dispersion liquid] is stirred with a tool like a spatula, and an ultrasonic homogenizer with an appropriate output may be radiated.

In the case of obtaining an inorganic metallic colloidal dispersion liquid containing a plurality of metals, its manufacturing method is not particularly limited, and for example, when the inorganic metallic colloidal dispersion liquid made from silver and other metal(s) is manufactured, in preparation of the inorganic metallic particles that are coated with organics, a dispersion liquid containing inorganic metallic particles and another dispersion liquid containing other inorganic metallic particles are separately manufactured and then, they can be mixed, and, a silver ion solution and an ion solution of other metal can be mixed and then, reduced.

(3) Joining Method

If the bonding composition of the present embodiment, high joint strength can be obtained in joining of members each other in association with heating. In other words, a first member to be joined and a second member to be joined can be joined with a bonding composition application step to apply the bonding composition between the first member to be joined and the second member to be joined and a joining step to bake and join the bonding composition applied between the first member to be joined and the second member to be joined at a desired temperature (for example, at 300° C. or less, preferably at 150° C. to 200° C.). On this occasion, pressure can be applied, but it is one of the advantages of the present invention to enable the obtainment of sufficient joint strength without particular pressurization. Further, on the occasion of baking, the temperature can be increased and decreased in a step-by-step manner. Further, it is also possible to apply a surfactant, a surface-activation agent or the like on the surfaces of the members to be joined in advance.

The inventors of the present application, as a result of keen study, have discovered that the first member to be joined and the second member to be joined can be more certainly joined with high joint strength (a joined body can be obtained) if the bonding composition of the present embodiment is used as a bonding composition in the application step of a bonding composition.

Herein, "application" of the bonding composition of the present embodiment is a concept including a case of applying (drawing) the bonding composition planarly or linearly. It is possible to modify the shape of a coating film made from the bonding composition under the condition before applying and baking by heating to a desired level. Therefore, in the joined body of the present invention after baking by heating, the bonding composition is a concept including a planar joining layer and a linear joining layer, and these planar joining layer and linear joining layer can be continuous or discontinuous, and can contain a continuous portion and a discontinuous portion.

As the first member to be joined and the second member to be joined that can be used in the present embodiment, anything is acceptable as long the bonding composition can be applied and baked by heating and these can be joined and they are not particularly limited, and members that are equipped with heat resistance to some degree not to be damaged at temperature upon joining are preferable.

As materials composing such members to be joined, for example, polyester, such as polyamide (PA), polyimide (PI), polyamide-imide (PAI), polyethylene terephthalate (PET), polybutylene terephthalate (PBT) or polyethylene naphthalate (PEN); polycarbonate (PC), polyether sulfone (PES), vinyl resin, fluorine resin, liquid crystal polymer, ceramics, glass, metal and the like can be exemplified, and metallic members to be joined are preferable among these. The reason why the metallic members to be joined are preferable is because they excel in heat resistance, and, excel in affinity with the bonding composition of the present invention where inorganic particles are metal.

Further, the members to be joined can be various shapes, such as plate-state or strip-state, and they can be rigid or flexible. Thickness of a substrate can be appropriately selected. For the purpose of improvement of adhesion properties or adhesiveness or for other purposes, a member where a surface layer is formed and a member where surface treatment, such as hydrophillic treatment, has been applied may be used.

In the step to apply the bonding composition onto the members to be joined, it is possible to use various methods, and as mentioned above, for example, the method can be appropriately selected and used from dipping, screen printing, a spray method, a bar coating technique, a spin coating technique, an inkjet technique, a dispenser technique, a pin transfer technique, an application method with a brush, a casting technique, a flexo technique, a gravure technique, a syringe technique and the like.

The coating film after being applied as mentioned above is baked by heating to a temperature of 300° C. or less within a range not damaging the members to be joined, and the joined body of the present embodiment can be obtained. In the present embodiment, as mentioned above, because the bonding composition of the present embodiment is used, a joining layer having adhesiveness toward the members to be joined, and strong joint strength can be more certainly obtained.

In the present embodiment, when the bonding composition contains a binder component, the binder component shall also be sintered from viewpoints of improvement of strength of the joining layer and improvement of the joint strength between the members to be joined, but the binder component can be all removed by controlling the baking conditions by regarding the adjustment of viscosity of the bonding composition as a main purpose in order to apply to various printing methods according to circumstances.

The method for baking is not particularly limited, but [the members to be joined] can be joined by baking to, for example, 300° C. or less of the temperature of the bonding composition applied or drawn onto the members to be joined, for example, using a conventionally-known oven or the like. The lower limit of the baking temperature is not necessarily limited, but it is preferable that the temperature is a temperature enabling to join the members to be joined with each other, and, is a temperature within the range not impairing the effects of the present invention. Herein, in the bonding composition after baking, the smaller a residue of organics becomes the better from a point of achieving higher joint strength as much as possible, but part of the organics can remain within the range not impairing the effects of the present invention.

Furthermore, although the bonding composition of the present invention contains organics, unlike a conventional one by utilizing thermal curing, such as epoxy resin, the joint strength after baking is not obtained due to the functions of the organics, but sufficient joint strength can be obtained due to fusion of fused inorganic metallic particles. Consequently, after joining, even if the residual organics are deteriorated or decomposed/disappeared due to placement under a use environment of higher temperature than the joining temperature, the joint strength shall not be decreased; therefore, [the bonding composition] excels in heat resistance.

According to the bonding composition of the present embodiment, since the joint having a joining layer to develop high conductivity can be realized even with baking by low-temperature heating at, for example, approximately 150° C. to 200° C., members to be joined that are comparatively weak against heat can be joined. Further, the baking time is not particularly limited, but a baking time enabling joining according to the baking temperature is acceptable.

In the present embodiment, in order to further enhance adhesiveness between the members to be joined and the joining layer, a surface treatment can be applied to the members to be joined. As the surface treatment method, for example, a method for dry treatment, such as corona treatment, plasma treatment, UV treatment or electron beam treatment; a method to establish a primer layer or a conductive paste receptive layer onto a substrate in advance and the like are exemplified.

Thus, the typical embodiments of the present invention were explained, but the present invention should not be limited to these only. For example, in the embodiments above, the inorganic metallic colloidal dispersion liquid where metallic particles are adopted as inorganic particles was explained, but inorganic particles, such as tin-doped indium oxide, alumina, barium titanate or phosphoric acid iron lithium, excelling in, for example, conductivity, thermal conductivity, ion conductivity or the like, can be used, as well.

Hereafter, the bonding composition of the present invention will be further explained in examples, but the present invention shall not be limited to these examples, at all.

EXAMPLES

Example 1

Hexylamine (EP grade manufactured by Tokyo Chemical Industry Co., Ltd.) (50 g) was added to 300 mL of toluene (special grade manufactured by Wako Pure Chemical Industries, Ltd.), and [a mixture] was stirred well with a magnetic stirrer. While stirring, 10 g of silver nitrate (special grade manufactured by Wako Pure Chemical Industries, Ltd.) was added, and when silver nitrate was dissolved, 10 g of oleic acid (first class grade manufactured by Wako Pure Chemical Industries, Ltd.) and 5 g of hexane acid (special grade manufactured by Wako Pure Chemical Industries, Ltd.) were sequentially added, and silver nitrate in a toluene solution was prepared.

After stirring sufficiently to remove heat, 0.02 g/mL of sodium borohydride aqueous solution that was prepared by adding 2 g of sodium borohydride to 100 mL of ion-exchanged water was instilled into this silver nitrate in a toluene solution, and stirring was continued for one hour and silver particles were generated. Then, 500 mL of methanol (special grade manufactured by Wako Pure Chemical Industries, Ltd.) was added and the silver particles were settled. In addition, after the silver particles were completely settled by centrifugal separation, a reaction residue, a solvent(s) and the like contained in a supernatant were removed.

Sediments (untreated silver particle composition) containing remaining silver particles after the removal of the supernatant were depressurized for several minutes using a diaphragm pump, and after a small amount of residual methanol was evaporated well, [the sediments] were thermally treated by placing into an oven at 200° C. for 20 minutes under the atmosphere, and a silver particle composition 1 where amounts of organics including hexylamine, oleic acid and hexane acid were adequately reduced was obtained.

[Measurement of Joint Strength]

The bonding composition 1 was obtained by adding 1 g of ricinoleic acid (for chemistry manufactured by Wako Pure Chemical Industries, Ltd.) to 5 g of the silver particle composition 1, and by stirring and mixing well. A small amount of the bonding composition was placed onto an alumina plate (50 mm square) where its surface was gold-plated using a die bonder (manufactured by HiSOL, Inc.), and a commercially-available blue LED chip (manufactured by GeneLite Inc.; bottom area 600 microns×600 microns) was mounted over it. On that occasion, no pressure was applied by adding external force.

Then, the obtained mounted body was placed into a dry air oven adjusted at 200 ° C., and was baked by heating for 120 minutes under the atmosphere. After the mounted body was extracted and cooled, a joint strength test (sheer height: 10 microns from the substrate, sheer tool rate: 0.01 mm/sec) was conducted using a bond tester (PTR-1101 manufactured by Rhesca Corporation) at room temperature. The joint strength upon peeling was converted using a bottom area of the chip. Numerical numbers in the evaluation results are MPa notation.

Example 2

A bonding composition 2 was prepared as similarly to Example 1 except for not adding ricinoleic acid, and joint strength was measured. Results are shown in Table 1.

Example 3

A bonding composition 3 was prepared as similarly to Example 1 except for using ricinoleic acid instead of oleic acid, and joint strength was measured. Results are shown in Table 1.

Example 4

A bonding composition 4 was prepared as similarly to Example 1 except for not further adding ricinoleic acid to the silver particle composition obtained by using ricinoleic acid instead of oleic acid, and joint strength was measured. Results are shown in Table 1.

Comparative Example 1

A comparative bonding composition 1 was prepared as similarly to Example 1 except for not adding oleic acid and ricinoleic acid, and joint strength was measured. Results are shown in Table 1.

Comparative Example 2

A comparative bonding composition 2 was prepared as similarly to Example 1 except for using dodecylamine instead of hexylamine and then not adding ricinoleic acid, and joint strength was measured. Results are shown in Table 1.

Comparative Example 3

A comparative bonding composition 3 was prepared as similarly to Example 1 except for using oleylamine instead of hexylamine and then, not adding ricinoleic acid, and joint strength was measured. Results are shown in Table 1.

TABLE 1

| | | Joint strength. at 200° C. | Unsaturated fatty acid | Amine |
|---|---|---|---|---|
| Examples | 1 | 20.1 | Oleic acid, ricinoleic acid | Hexylamine |
| | 2 | 14.8 | Oleic acid | Hexylamine |
| | 3 | 21.3 | Ricinoleic acid | Hexylamine |
| | 4 | 18.9 | Ricinoleic acid | Hexylamine |
| Comparative Examples | 1 | 0.5 | None | Hexylamine |
| | 2 | 2.2 | Oleic acid | Dodecylamine |
| | 3 | 1.4 | Oleic acid | Oleylamine |

According to the results shown in Table 1, even though the joining temperature is a low temperature at 200° C. in the examples of the present invention, and even though this was joining under a pressureless condition, high joint strength around 20 MPa is indicated. In the meantime, in the case of using the bonding composition that is not equipped with the configuration of the present invention, the joint strength is extremely low under the similar joining conditions.

What is claimed is:

1. A bonding composition, comprising:
   inorganic metallic particles and
   organic components including unsaturated carboxylic acid and amine having a carbon number of 4 to 7 and a boiling point of 300° C. or less.

2. The bonding composition according to claim 1, wherein the unsaturated carboxylic acid is ricinoleic acid.

3. The bonding composition according to claim 1, wherein the organic components are attached to at least a part of a surface of each of the inorganic metallic particles.

4. The bonding composition according to claim 1, wherein the inorganic metallic particles have a particle size of 1 nm to 200 nm.

5. The bonding composition according to claim 1, wherein the inorganic metallic particles have a particle size of 2 nm to 100 nm.

6. The bonding composition according to claim 1, wherein the inorganic metallic particles are selected from the group consisting of gold, silver, copper, nickel, bismuth, tin, ruthenium, rhodium, palladium, osmium, iridium and platinum.

7. The bonding composition according to claim 1, wherein the amine is selected from the group consisting of butylamine, pentylamine, hexylamine, cyclopentylamine, cyclohexylamine, allylamine, aniline, dipropylamine, dibutylamine, piperidine, hexamethyleneimine, tripropylamine, dimethyl propanediamine, cyclohexyldimethylamine, and pridine.

8. The bonding composition according to claim 1,
   wherein the organic components further comprises a carboxyl acid, and
   wherein the carboxyl acid is selected from the group consisting of formic acid, oxalic acid, acetic acid, hexane acid, acrylic acid, octylic acid and oleic acid.

9. The bonding composition according to claim 1, wherein the content of the organic components is 0.5% to 50% by mass.

10. The bonding composition according to claim 1, wherein the content of the organic components is 2% to 15% by mass.

11. The bonding composition according to claim 1, wherein the organic components further comprises an unsaturated hydrocarbon, and
   wherein the unsaturated hydrocarbon is selected from the group consisting of ethylene, acetylene, benzene, acetone, 1-hexene, 1-octene, 4-vinylcyclohexene, cyclohexanone, terpene-series alcohol, allyl alcohol, oleyl alcohol, 2-palmitoleic acid, petroselinic acid, oleic acid, elaidic acid, tianshic acid, linoleic acid, linolelaidic acid, linolenic acid, arachidonic acid, acrylic acid, methacrylic acid, gallic acid and salicylic acid.

12. The bonding composition according to claim 1, further comprises an optional component, wherein the optional component is selected from the group consisting of a binder, a resin component, an organic solvent, a surfactant, a thickener and a surface tension regulator.

13. The bonding composition according to claim 1, wherein the bonding composition has a viscosity of 0.01 Pa·s to 5,000 Pa·s.

14. The bonding composition according to claim 4, wherein the bonding composition has a viscosity of 1 Pa·s to 100 Pa·s.

* * * * *